US011229390B2

(12) United States Patent
Myllykangas

(10) Patent No.: US 11,229,390 B2
(45) Date of Patent: Jan. 25, 2022

(54) ELECTRODE DEVICE

(71) Applicant: Bittium Biosignals Ltd, Kuopio (FI)

(72) Inventor: Juha Matti Myllykangas, Kuopio (FI)

(73) Assignee: BITTIUM BIOSIGNALS LTD, Kuopio (FI)

(*) Notice: Subject to any disclaimer, the term of this patent is extended or adjusted under 35 U.S.C. 154(b) by 941 days.

(21) Appl. No.: 15/966,785

(22) Filed: Apr. 30, 2018

(65) Prior Publication Data

US 2019/0328252 A1    Oct. 31, 2019

(51) Int. Cl.
| | | |
|---|---|---|
| *A61B 5/04* | (2006.01) | |
| *A61B 5/25* | (2021.01) | |
| *H05K 1/02* | (2006.01) | |
| *H05K 1/09* | (2006.01) | |
| *H05K 1/11* | (2006.01) | |
| *H05K 1/18* | (2006.01) | |
| *H05K 5/06* | (2006.01) | |
| *A61B 5/291* | (2021.01) | |

(52) U.S. Cl.
CPC .............. *A61B 5/25* (2021.01); *A61B 5/291* (2021.01); *H05K 1/028* (2013.01); *H05K 1/09* (2013.01); *H05K 1/111* (2013.01); *H05K 1/181* (2013.01); *H05K 5/065* (2013.01)

(58) Field of Classification Search
CPC .......... A61B 5/25; A61B 5/291; H05K 1/028; H05K 1/09; H05K 1/111; H05K 1/181; H05K 5/065
USPC ....................................................... 600/372
See application file for complete search history.

(56) References Cited

U.S. PATENT DOCUMENTS

| | | | | |
|---|---|---|---|---|
| 9,277,864 B2 * | 3/2016 | Yang | ................ | A61B 5/6833 |
| 2013/0213147 A1 * | 8/2013 | Rice | ................ | A43B 7/088 |
| | | | | 73/862.046 |
| 2020/0187859 A1 * | 6/2020 | Yoshioka | ........... | A61B 5/6833 |

FOREIGN PATENT DOCUMENTS

| | | |
|---|---|---|
| FR | 2692351 A1 | 12/1993 |
| KR | 10-2008-0039697 A | 4/2018 |
| WO | 2014/057083 A2 | 4/2014 |

OTHER PUBLICATIONS

Extended European Search Report issued in European Patent Application No. 19170120.0 dated Oct. 4, 2019.

* cited by examiner

*Primary Examiner* — Binh B Tran
(74) *Attorney, Agent, or Firm* — Nixon & Vanderhye

(57) ABSTRACT

Disclosed is an electrode device for measuring an electric biosignal. The electrode device includes a flexible PCB (printed circuit board) having a flexible support layer and a trace layer on a first side. The trace layer includes at least two electrode pads for skin contacts and, for each electrode pad, a solder pad and a conducting trace forming a galvanic connection between the electrode and the solder pad. The flexible PCB further includes an opening defining a flexible, elongated cantilever in a central portion of the flexible PCB, having a base end connected to the central portion and a free end separated from the central portion. The solder pads are located at the free end. The electrode device further includes a connector component on the second side, soldered to the solder pads on the free end of the cantilever.

6 Claims, 2 Drawing Sheets

ELECTRODE DEVICE

FIELD

The invention relates to measurement of biosignals, and in particular, to measurement of electric biosignals with low-cost, flexible electrodes.

BACKGROUND INFORMATION

Low-cost, flexible electrodes are typically PET-based (Polyethylene terephthalate) structures with AgCl-based (silver chloride) electrodes. However, such electrodes break easily and do not tolerate well bending that occurs during normal use. Further, signal quality from such electrodes degrades quickly over time. Therefore, AgCl+PET electrodes are not well suited for longer measurements.

BRIEF DISCLOSURE

An object of the present disclosure is to provide an electrode device so as to alleviate the above disadvantages. This object is achieved by an electrode device which is characterized by what is stated in the independent claim. The preferred embodiments of the disclosure are disclosed in the dependent claims.

A flexible PCB (printed circuit board) may be used as a basis for a cost-efficient, robust electrode device. Electrodes solder pads for a connector, and traces connecting the electrodes and the solder pads may be formed on a single side of the PCB. The connector serves as an interface for forming a galvanic connection between the electrodes and measurement electronics.

The PCB may comprise a cantilever formed to the PCB, and the solder pads for the connector may be positioned to the tip of the cantilever. As the cantilever is formed out of the flexible PCB, the cantilever is able to bend, and therefore, the connector can be positioned on an opposite side of the electrodes. In this manner, a compact device with electrodes on one side and a connector on the other can be cost-efficiently formed with a single-sided PCB.

Further, the electrodes, traces, and solder pads may be made of copper, for example, and provided with a gold-plating and a solder mask leaving only the electrodes and solder pads exposed. This provides low-impedance connections between the electrodes and the solder pads, thereby improving signal quality. The gold plating also makes the electrode device less susceptive to corrosion so that the electrode device is able to maintain its good signal characteristics longer. The gold-plating may be formed before the solder mask, and the openings for the electrodes in the solder mask may be made smaller than the electrodes so that the solder mask overlaps the electrodes in the periphery of the electrodes. In this manner, when the electrode device is attached to skin of a person, only gold plated surfaces of the electrodes are in contact with the skin, and skin irritation can be minimized. Further, the above-described structure maximizes water resistance, thereby further increasing the operating time.

The PCB-based structure is also very robust. The copper traces and the gold plating can withstand bending well, and therefore the electrode device is not prone to breaking e.g. during movements of skin and/or removal of measurement electronics for recharging.

BRIEF DESCRIPTION OF THE DRAWINGS

In the following the invention will be described in greater detail by means of preferred embodiments with reference to the attached drawings, in which.

DETAILED DISCLOSURE

The present disclosure describes an electrode device for measuring an electric biosignal. In the context of the present disclosure, an electric biosignal may be a signal that can be consistently, non-invasively measured and monitored from a human body with electrodes. Electroencephalography (EEG) and electrocardiography (ECG) are examples of electrical biosignals.

Figure 1A:
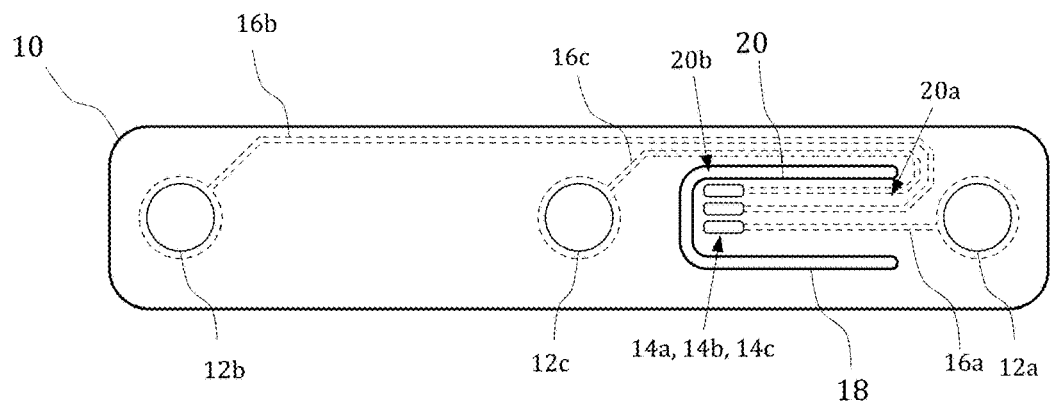
FIGS. 1a to 1d show simplified views of an embodiment of electrode device according to the present disclosure.

An electrode device according to the present disclosure comprises flexible PCB (printed circuit board) having at least a flexible support layer and a trace layer on a first side of the flexible PCB, and a connector component on an second side of the flexible PCB opposite to the first side. FIGS. 1a to 1d show simplified views of an embodiment of electrode device according to the present disclosure. FIG. 1a shows a bottom view of a flexible PCB 10 without a connector. The PCB 10 is in the form of an elongated, rectangular strip. The length of the PCB may be at least three times the width of the PCB, for example. The length may be 10 cm to 20 cm and the width may be 12 mm to 30 mm, for example.

A flexible PCB of an electrode device according to the present disclosure may be formed to be very thin. In this manner, the electrode device can be made slack so that it is able to easily adjust to movements of the skin. The thickness of the PCB may be less than one tenth (5%) of the width, or even less than one hundredth (1%) of the width, for example. The thickness may be less than 0.3 mm for example. In a preferred embodiment, the length is in the range of 12 cm to 18 cm; the width is in the range of 15 mm to 21 mm; and the thickness is in the range of 0.14 mm to 0.20 mm.

The trace layer of the flexible PCB of an electrode device according to the present disclosure may comprise the trace layer comprising at least two electrode pads for skin contacts and, for each electrode pad, a solder pad and a conducting trace for forming a galvanic connection between the electrode and the solder pad. The electrode pads, solder pads, and the traces may be made of copper, for example. In FIG. 1a, three electrode pads 12a to 12c and three solder pads 14a to 14c are shown on the first side of the PCB 10. A first electrode pad 12a at one end of the flexible PCB 10, a second electrode pad 12b on the opposite end of the PCB 10 and a third electrode 12c pad between the first electrode pad 12a and second electrode pad 12b. Traces 16a to 16c between the electrodes 12a to 12c and the solder pads 14a to 14c, respectively, are shown with dashed lines as they are covered by a solder mask layer. In some embodiments, the trace layer may be provided with a gold plating prior to providing the solder mask layer. The gold-plated trace layer may then be provided with the solder mask layer such that the solder mask layer overlaps over the electrode pads in peripheries of the electrode pads. In this manner, only gold-plated centre portions of the electrode pads are exposed to skin contact and/or to electrode gel that may have been applied to ensure the skin contact. Further, the solder mask partially overlapping the electrode pads prevents the electrode pads from detaching from the flexible PCB.

In FIG. 1a, the galvanic connections are in the form of continuous conducting traces between the electrodes and the solder pads. However, in addition to the conducting traces, the galvanic connections may also comprise passive components, such as surface-mount resistors. Thus, the galvanic connection may be formed by the traces and passive components together. The trace layer may therefore further comprise solder pads for said passive components. The resistors may serve as fault protection devices, for example. High resistance resistors may be connected between each electrode pad and the corresponding connector solder pad, for example. In this manner, any fault current from the measurement electronics to the person wearing the electrode pad remains small. Any currents from the person to the measurement electronics during the use of a defibrillator, for example, also remain small.

In addition, the flexible PCB may also comprise additional solder pads for ground contacts of the connector and/or for anchoring the connector in place.

In an electrode device according to the present disclosure, the flexible PCB may comprise an opening through the layers so that the opening forms an open loop in a plane of the layers. The open loop defines a flexible, elongated cantilever in a central portion of the flexible PCB. The flexible cantilever may have a base end connected to the central portion and a free end separated from the central portion. The solder pads for the connector may be located at the free end. In FIG. 1a, the open loop is a U-shaped form 18 located between the first electrode pad 12 and third electrode pad 12c and opens towards the first electrode pad 12a. The U-shaped opening defines an elongated, flexible cantilever 20 that has a base end 20a connected to the PCB 10 and a free end 20b. The cantilever has a length that is at least twice its width. In FIG. 1a, the length of the cantilever 20 extends in the same direction as the length of the PCB 10. The connector solder pads 14a to 14c are positioned at the free end 20b in FIG. 1a.

Figure 1B:
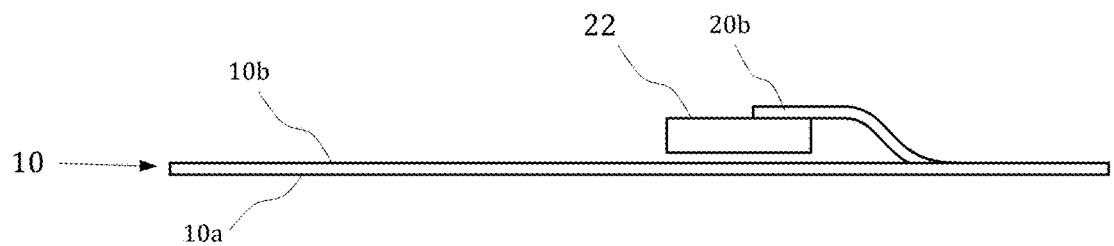

In an electrode device according to the present disclosure, the free end of the flexible cantilever bends to the second side of the flexible PCB opposite to the first side having the electrode pads. The electrode device further comprises a surface-mount connector component on the second side, soldered to the solder pads on the free end of the cantilever. FIG. 1b shows a side view of the PCB 10 of FIG. 1a, now provided with a connector component 22. In FIG. 1b, a first side 10a of the PCB 10 is facing downwards and a second side with the connector 22 is facing upwards. The electrodes (not shown in FIG. 1b) are on the first side 10a and the connector 22 is on the second side 10b. One end of the connector component 22 is between the second side 10b and the free end 20b f the cantilever. The solder pads 14a to 14c (not shown in FIG. 1b) are on the first side, i.e. the surface facing down, of the free end 20b in FIG. 1b. The connector component 22 has corresponding contacts (not shown in FIG. 1b) on the facing upwards, i.e. facing the first side of the free end 20b, in FIG. 1b.

In some embodiments of an electrode device according to the present disclosure, the connector component may be a connector configured to be detachably attached to a corresponding connector component of a measurement unit, thereby forming a galvanic connection between the electrode pads and measurement electronics of the measurement unit. The connector component may be a standard computer interface connector, such as a surface-mount micro-USB connector component, for example. The measurement unit may be a self-powered, portable measurement unit, for example. The measurement unit may be configured to measure EEG and/or ECG, for example.

Figure 1C:
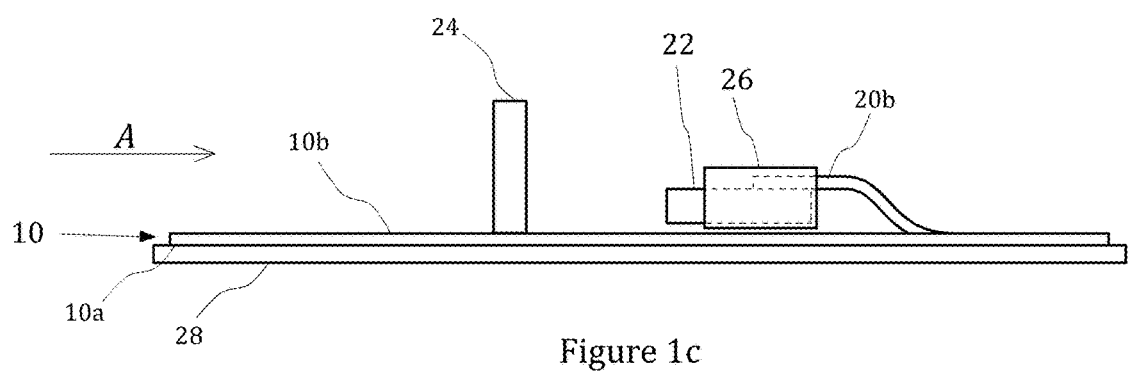
Figure 1D:
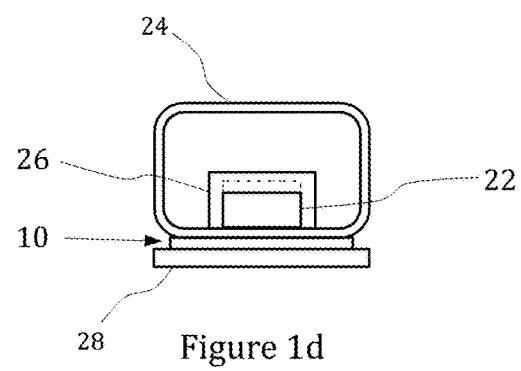

In some embodiments of an electrode device according to the present disclosure, the electrode device may further comprise a docking element on the second side of the flexible PCB. The docking element may be configured to receive a measurement module therein and holding the measurement module in place when the connector of the electrode device is connected to the connector of the measurement unit. FIG. 1c shows a side view of an embodiment similar to the embodiments of FIGS. 1a and 1b. FIG. 1d shows a front view of the embodiment of FIG. 1c. The view direction of FIG. 1d is shown with arrow A in FIG. 1c. In FIGS. 1c and 1d, the electrode device comprises a docking element in the form of a flexible loop 24. The loop may be made of transparent plastics, for example. In this manner, any visual elements, such as LEDs, of the measurement unit can be seen even when the loop 24 encircles the measurement unit.

An electrode device according to the present disclosure may also comprise a protective coating around the connector. In FIGS. 1c and 1d, a part of the connector 22 and the free 20b end of the cantilever are both encased in a waterproof, insulating coating 26. In this manner, the water resistance of the electrode device can be improved. In addition, an electrode device according to the present disclosure may also comprise one or additional layers attached to the first side of the flexible PCB. FIGS. 1c and 1d show an additional layer 28 which may in practice be one or more layers. The one or more additional layer may comprise a cushion layer that may be attached to the first side of the flexible PCB, for example. The cushion layer may have holes at the locations of the electrode pads. Electrode gel may be deposited at these holes in order to ensure a good connection between the electrode pads and the skin of a person. The outmost layer of the one or more additional layers on the first side of the flexible PCB may be an adhesive layer enabling easy attachment of the electrode device to the skin. In this manner, an embodiment of a self-adhesive electrode device according to the present disclosure can be achieved.

The following paragraphs discuss some aspects of manufacturing an electrode device according to the present disclosure. Said aspects are discussed in reference to FIG. 2 that shows a simplified flow diagram of an exemplary manufacturing process of an electrode device according to the present disclosure.

Figure 2:
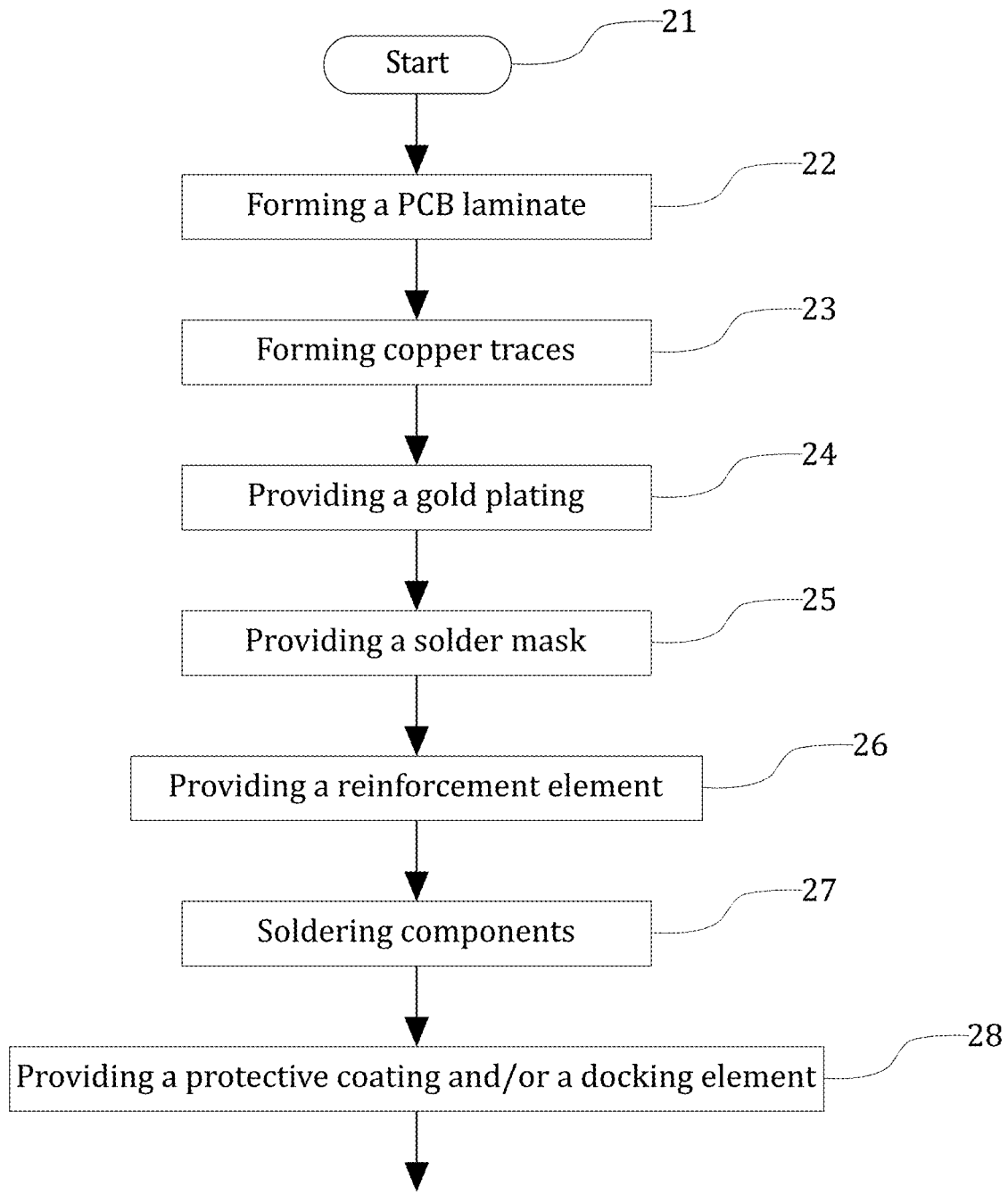
FIG. 2 shows a simplified flow diagram of an exemplary manufacturing process of an electrode device according to the present disclosure.

In FIG. 2, the manufacturing process begins at phase 21. Next, a PCB laminate is formed in phase 22, and conductive traces, electrode pads, and solder pads are formed on the laminate formed in phase 23. An electrode device according to the present disclosure can be made safe using biocompatible materials. For example, the support layer of the flexible PCB may be made of polyimide, and the traces and pads on the trace layer may be made of copper. Several flexible PCBs of an electrode device according to the present disclosure may be formed on a panel.

As discussed earlier, a gold-plating may be formed on the copper traces, solder pads, and electrode pads prior to providing a solder mask to the trace layer. In phase 24 of Figure, the conductive traces, electrode pads, and solder pads are gold plated, and then, in phase 25, the solder mask is being provided. The gold plating may be provided with ENIG (Electroless nickel immersion gold) or flash plating process, for example. The solder mask has openings at the locations of the electrode pads, but these openings may be formed smaller than the electrode pads so that the solder mask overlaps the edges of the electrode pads.

In some embodiments, the flexible PCB may be provided with a reinforcement element (i.e. a stiffener) in order to facilitate mounting and soldering of components to the solder pads. In FIG. 2, a reinforcement element is provided in phase 26. The flexible PCBs may have been arranged into rows on the panel such that the solder pads on the first side of the flexible PCBs align into a straight line, and the reinforcement element may be in the form of a thin strip running beneath the solder pads on the second side of the flexible, for example. The reinforcement element may be made of FR4 (glass-reinforced epoxy laminate) substrate material, for example.

The components may then be mounted on the flexible PCB. In FIG. 2, the components are soldered in phase 27. Preferably, the components used in an electrode device according to the present disclosure are surface-mount components, and said components are soldered to the PCB by using reflow soldering. With surface-mount components and reflow soldering, a particularly cost-efficient electrode device can be achieved.

Since the cantilever of the flexible PCB is also flexible, it can be bent out from the plane of the flexible PCB for further processing. For example, the cantilever can be inserted to a mould of an injection moulding machine. With injection moulding, at least part of a connector component and passive components at the free end of the cantilever, and a part of the free end itself may be encased in a waterproof protective coating. In some embodiments, a portion of the reinforcement element may remain attached to the flexible PCB in order to facilitate the injection moulding. The reinforcement element may be provided with breakaway perforations defining the portions that remain attached to the PCB. These portions may become encased in the protective coating together with the part of the connector component, the passive components, and the part of the free end. A docking element for the measurement unit may also be formed with injection moulding. In FIG. 2, a protective coating is provided in phase 28. The manufacturing process may also comprise further phases. For example, the process may include additional phases after phase 28 and/or phases between phases 21 to 28.

It is obvious to a person skilled in the art that the electrode patch and the detection method/system can be implemented in various ways. The invention and its embodiments are not limited to the examples described above but may vary within the scope of the claims.

The invention claimed is:

1. An electrode device for measuring an electric biosignal, wherein the electrode device comprises:
   a) a flexible PCB (printed circuit board) having
      at least a flexible support layer and a trace layer on a first side of the flexible PCB, the trace layer comprising at least two electrode pads for skin contacts and, for each electrode pad, a solder pad and a conducting trace for forming a galvanic connection between the electrode and the solder pad, and
      an opening through the layers, wherein the opening defines a flexible, elongated cantilever in a central portion of the flexible PCB such that the flexible cantilever has a base end connected to the central portion and a free end separated from the central portion, wherein the solder pads are located at the free end and the free end bends to a second side of the flexible PCB opposite to the first side, and
   b) a connector component on the second side, soldered to the solder pads on the free end of the cantilever,
   wherein the trace layer is provided with a gold plating, and the gold-plated trace layer is provided with a solder mask layer that overlaps over the electrode pads in peripheries of the electrode pads such that only gold-plated center portions of the electrode pads are exposable to the skin contact.

2. The electrode device according to claim 1, wherein,
   the flexible PCB is in the form of an elongated strip,
   the at least two electrode pads comprise a first electrode pad at one end of the flexible PCB, a second electrode pad on the opposite end of the strip and a third electrode pad between the first and second electrode pad, and
   the opening is a U-shaped form located between the first and third electrode pad and opening towards the first electrode pad.

3. The electrode device according to claim 1, wherein
   the connector component is a surface-mount connector component configured to be detachably attached to a corresponding connector component of a portable measurement unit, thereby forming a galvanic connection between the electrode pads and measurement electronics of the measurement unit.

4. The electrode device according to claim 3, wherein the electrode device further comprises:
   c) a docking element on the second side of the flexible PCB for receiving the measurement module therein and holding the measurement module in place when the connector of the electrode device is connected to the connector of the measurement unit.

5. The electrode device according to claim 1, wherein,
   the connector component of the electrode device is a surface-mount standard computer interface connector component, and
   at least a portion of the connector component and the free end of the cantilever are both encased in a waterproof, insulating coating.

6. The electrode device according to claim 4,
   wherein the docking element is in the form of a transparent, flexible loop that encircles the measurement unit when received therein.

* * * * *